United States Patent
Msika et al.

(10) Patent No.: US 10,444,225 B2
(45) Date of Patent: Oct. 15, 2019

(54) SURFACE ISOTROPY AS A MARKER FOR EPIDERMAL MATURATION

(71) Applicant: LABORATOIRES EXPANSCIENCE, Courbevoie (FR)

(72) Inventors: Philippe Msika, Versailles (FR); Nadège Lachmann, Checy (FR); Joachim Fluhr, Berlin (DE)

(73) Assignee: LABORATOIRES EXPANSCIENCE, Paris la Defense (FR)

( * ) Notice: Subject to any disclaimer, the term of this patent is extended or adjusted under 35 U.S.C. 154(b) by 335 days.

(21) Appl. No.: 14/418,645

(22) PCT Filed: Aug. 2, 2013

(86) PCT No.: PCT/EP2013/066332
§ 371 (c)(1),
(2) Date: Jan. 30, 2015

(87) PCT Pub. No.: WO2014/020173
PCT Pub. Date: Feb. 6, 2014

(65) Prior Publication Data
US 2015/0153328 A1 Jun. 4, 2015

Related U.S. Application Data

(60) Provisional application No. 61/678,780, filed on Aug. 2, 2012.

(30) Foreign Application Priority Data

Feb. 18, 2013 (EP) ..................................... 13305181

(51) Int. Cl.
*G01N 33/50* (2006.01)

(52) U.S. Cl.
CPC ..... *G01N 33/5044* (2013.01); *G01N 33/5085* (2013.01); *G01N 2500/10* (2013.01)

(58) Field of Classification Search
None
See application file for complete search history.

(56) References Cited

FOREIGN PATENT DOCUMENTS

FR 2785170 A1 5/2000

OTHER PUBLICATIONS

Kim, Dong-Kun, and Karen A. Holbrook. "The appearance, density, and distribution of Merkel cells in human embryonic and fetal skin: their relation to sweat gland and hair follicle development." Journal of investigative dermatology 104.3 (1995): 411-416.*
Dawber, Rodney PR, Ronald Marks, and J. Swift. "Scanning electron microscopy of the stratum corneum." British Journal of Dermatology 86.3 (1972): 272-281.*
Hani, Ahmad, et al. "High order polynomial surface fitting for measuring roughness of psoriasis lesion." Visual Informatics: Sustaining Research and Innovations (2011): 341-351.*
Ramsay, B., and C. M. Lawrence. "Measurement of involved surface area in patients with psoriasis." British Journal of Dermatology 124.6 (1991): 565-570.*
Montagna, William, and Kay Carlisle. "Structural changes in aging human skin." Journal of Investigative Dermatology 73.1 (1979): 47-53. (Year: 1979).*
Hull, Meredith T., and K. A. Warfel. "Age-Related Changes in Cutaneous Basal Lamin: Scanning Electron Microscopic Study." Journal of investigative dermatology 81.4 (1983): 378-380. (Year: 1983).*
Tsuji, Takuo, and Toshio Hamada. "Age-related changes in human dermal elastic fibres." British Journal of Dermatology 105.1 (1981): 57-63. (Year: 1981).*
Tinkle, Sally S., et al. "Skin as a route of exposure and sensitization in chronic beryllium disease." Environmental health perspectives 111.9 (2003): 1202. (Year: 2003).*
Pagnoni, A., et al. "Determination of density of follicles on various regions of the face by cyanoacrylate biopsy: correlation with sebum output." British Journal of Dermatology 131.6 (1994): 862-865. (Year: 1994).*
Hoeger, et al. "Skin Physiology of the Neonate and Young Infant: A Prospective Study of Functional Skin Parameters During Early Infancy" Pediatric Dermatology (May 1, 2002) vol. 19, No. 3, pp. 256-262.
International Search Report in PCT/EP2013/066332 dated Sep. 23, 2013.
Leveque, "EEMCO guidance for the assessment of skin topography", Journal of the European Academy of Dermatology and Venereology (Mar. 1, 1999), vol. 12, No. 2, pp. 103-114.

* cited by examiner

*Primary Examiner* — Robert J Yamasaki
(74) *Attorney, Agent, or Firm* — Potomac Law Group, PLLC

(57) ABSTRACT

The present invention relates to a method for determining the isotropy of the skin surface of a subject, and hence the degree of maturation of the said skin surface, by examining various parameters reflecting the cell organization. Methods for identifying active agents, raw materials and formulation are also provided.

17 Claims, 6 Drawing Sheets

Figure 1:
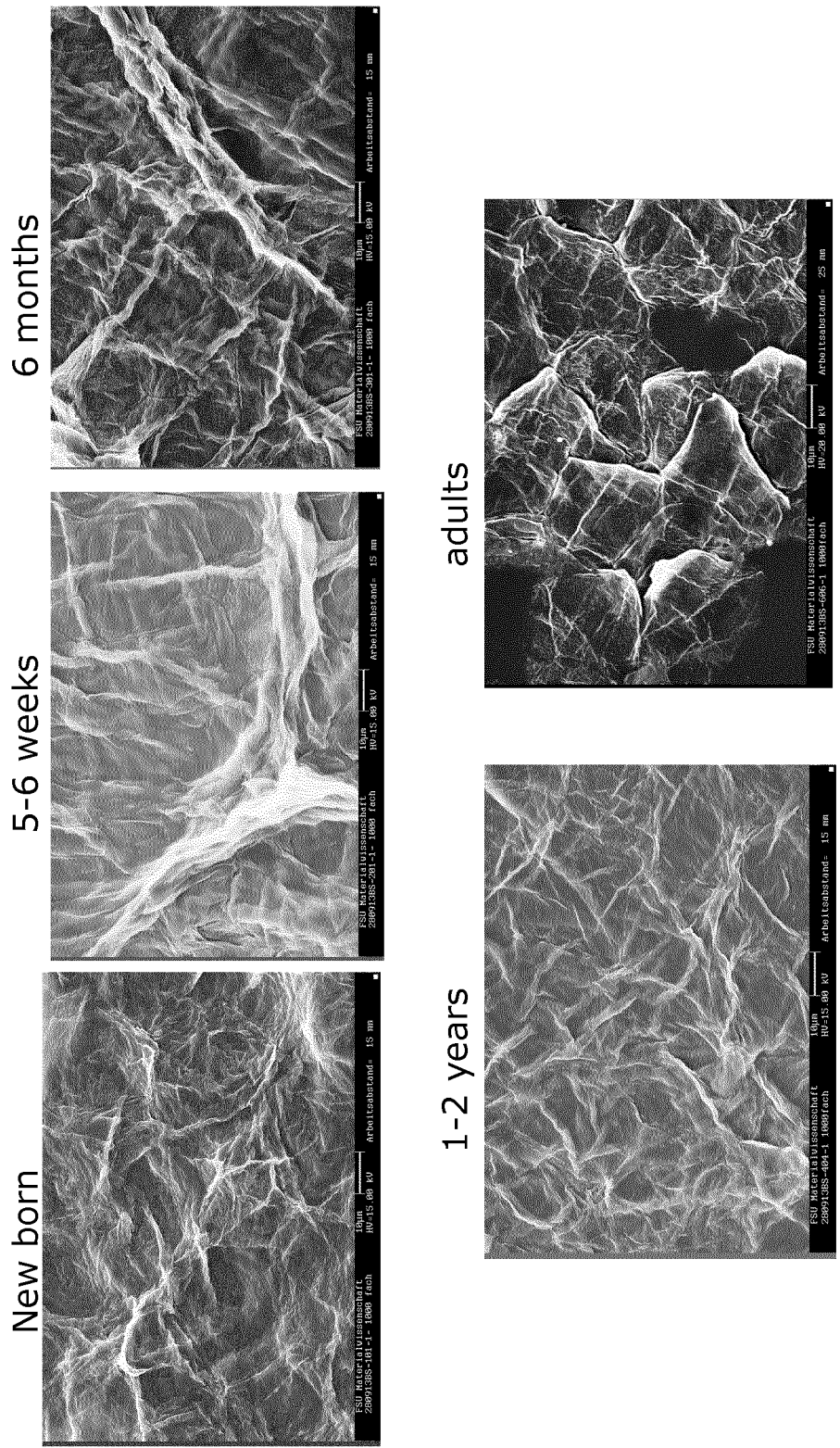

$Base\ Surface = Length \times Width \leq Relief\ Surface$ $Developed\ Surface = \dfrac{Relief\ Surface}{Base\ Surface}$

SURFACE ISOTROPY AS A MARKER FOR EPIDERMAL MATURATION

The skin is the largest organ of the human body and it has several functions. The most important is to protect the body against external influences.

The surface of the skin is not smooth, but is characterized by a particular relief reflecting the three-dimensional organization of the skin. This relief is subjected to changes due to both environmental and physiological factors. Among these factors, topical treatment by drugs and cosmetics is certainly of great importance.

The mechanical behaviour of skin is an important consideration in a number of cosmetic and clinical implications. For example, knowledge of its mechanical behaviour can help to quantify effectiveness of cosmetic products such as creams or lotions, and to study skin ageing. Finally, changes in mechanical properties of the skin due to skin diseases may play a role in a better understanding and treatment of these diseases.

In particular the barrier function of skin, which protects the body by preventing fluid loss and the penetration of undesirable substances, is primarily fulfilled by the top layer. This layer, also known as the stratum corneum, consists of the keratinocytes (constituted by proteins and lipids) embedded in a lipid rich matrix consisting of cholesterol, ceramides and fatty acids. Another class of lipids is also secreted at the surface of the epidermis which when in contact with the environment, interacts with water forming a hydrophilic film which is important for maintaining the moisture content and sensorial attributes of the skin. The lipid fraction of this hydrophilic film can also penetrate in the upper layer of the epidermis merging with the epidermal barrier and also contributing to its functions. This is an extremely important factor to consider when designing cosmetics, since it is the stratum corneum that interfaces with cosmetic products like creams and lotions.

Over the last decade, knowledge on newborn skin physiology has evolved. It is now clear that postnatal life is a time period of active functional maturation and cutaneous adaptation to the dry extra-uterine environment. Different environmental factors (for instance, dry and cold climate, diapers and cosmetic care procedures) influence the postnatal development of skin functional parameters such as stratum corneum hydration and the permeability barrier especially in premature infants.

The present inventor shave shown in a previous study (Fluhr et al., *Br J Dermatol*, 166(3): 483-90, 2012) that showed that the moisture and water content of the stratum corneum are lower at birth (infants 1 to 15 days), while the rate of natural moisturizing factor (NMF) is maximum. This rate then decreases while the hydration stabilizes. The authors hypothesize that the reduced acidification and lower hydration of the skin could activate regulatory mechanisms of compensation (including a significant production of NMF), which enables the newborn to adapt to his new environment.

In order to obtain a thorough assessment of the barrier function, one has to rely on parameters such as NMF, which require heavy technologies. In particular, the cost of the equipment for measuring NMF would prevent most biological laboratories from offering that kind of prestation.

There is thus still a need for the development of new tools for assessing the barrier function of the skin.

DESCRIPTION

The present inventors have shown that the level of maturation of the skin, and thus of its barrier organisation/function, can easily be determined by evaluating the isotropy/anisotropy of the skin surface. In this respect, the inventors have developed a new, semi-quantitative scoring system which enables to reliably and reproducibly assess the isotropy of the skin surface.

In order to elucidate the main cutaneous physiological functions in newborns, two clinical studies were performed. These studies aimed at investigating non-invasively skin surface maturation, by characterizing infant skin in comparison to different children age groups and adult's skin.

The present invention thus relates to a method for determining the degree of maturation of the skin surface of a subject. In particular, the present inventors have observed that the degree of maturation of the skin surface is closely correlated with increasing isotropy of the said skin surface, as estimated by examining various parameters reflecting the cell organization.

The method of the invention thus enables the characterization of the skin surface from birth and the monitoring of its evolution over time. A "child" means according to the invention an individual whose age is less than 16 years. In particular, are included within the category of children according to the invention, neonates of 1 to 15 days, infants of 5/6 weeks, infants of 6 months±1 month and infants of 1 to 2 years. A "neonate" as used herein, may as well be born at term as being premature. To avoid ambiguity, the term "child" used in this application without further explanation must be understood in its broadest sense, that is to say, as referring to a person under 16 years. An "adult" within the meaning of the present invention is a person who is not a child, i.e. a person aged over 16 years.

Preferably, the method of the invention can be used regardless of ethnicity or geographical skin, or phototype of it. It may well be of Caucasian, African, Asian, South American, Melanesian or any other origin; it can present a phototype I, II, III, IV, V or VI, without thereby affecting the invention. The method of the invention is indeed directed to the determination of skin surface maturation, regardless of the skin type, but depending only on donor age.

The present invention thus relates to a method for determining the degree of maturation of the skin surface of a subject, said method comprising a step of assessing the isotropy of the said skin surface.

By "anisotropy", it is herein referred to the property of being directionally dependent, whereas "isotropy", as used herein, implies identical properties in all directions. It is understood that isotropy and anisotropy are opposites, i.e. when isotropy increases, anisotropy decreases, whereas when anisotropy increases, isotropy decreases.

Skin is a highly non-linear, anisotropic, viscoelastic and nearly incompressible material. Its properties vary with age, from site to site and per person. This leads to difficulties in obtaining quantitative descriptions of mechanical properties of the skin. A second problem is the large variety of instruments, units and measurement conditions that was used which makes it hard to compare results.

The present inventors have found a new way of circumventing these inconvenient. They have observed that isotropy can be assessed by examining the cellular organization of the skin surface. According to this embodiment, the isotropy of the said skin surface is assessed by assessing cellular parameters such as cell density, cell clusters, adhesion/cell shape, and differentiability of single cells.

The present inventors have designed a new scoring system, the EMI (Electron Microscopy Isotropy) scoring system, which allows a semi-quantitative analysis of surface isotropy.

The said scoring system comprises the use of an appropriate scale based on 4 parameters which are the cell density, cell clusters, adhesion/cell shape, and differentiability of single cells. Each of these criteria is scored on a scale of 0 to 3, where 0 indicates that cells are separated, or that clusters are completely irregular, or that the shape of the cells is asymmetric and completely irregular, or that cells are not differentiable, while a score of 3 indicates that cells are confluent, or that clusters are regular, or that the shape of the cells is regular and symmetrical, or that cells are easily differentiable.

A score of 0-4 indicates anisotropy, while a score of 5-7 indicates intermediate isotropy, and a score of 8-12 indicates good isotropy.

It is thus possible to link the degree of maturation of the skin to the EMI score. A score of 0-4 indicates an immature skin surface, a score of 5-7 an intermediate maturity of the skin surface, and a score of 8-12 a fully mature skin surface.

On this basis, the inventors were able to distinguish three classes of skin surface maturation in relation to the age of the children:
immaturity: 0 to 5/6 weeks;
intermediate maturity: ≥5/6 weeks to 1-2 years; and
maturity: ≥1-2 years.

Thus in a preferred embodiment, the present invention relates to a method of determining whether the skin surface of a subject is mature or immature in its organisation/function, said method comprising the steps of:
 a) taking a skin sample (A) of the said subject;
 b) scoring the said skin sample to an appropriate scale, wherein the said appropriate scale is based on 4 parameters which are the cell density, cell clusters, adhesion/cell shape, and differentiability of single cells.

Preferably, the said scale is a scale of 0 to 12, wherein a score of 0 indicates strong anisotropy and a score of 12 indicates good isotropy.

The EMI score of the said skin surface sample can be determined to a reference obtained from the compilation of previous experimental results. Indeed, as shown by the present inventors, it is clear that the EMI score increases with age. For example, an EMI score of 4 or below is associated with an immature skin surface, whereas a score of 8 or more is associated with a mature skin surface.

Alternatively, it is possible to compare the EMI score of the skin surface sample of the invention with the EMI score of a skin surface sample from a reference subject. By "reference subject", it is herein meant a subject whose age is known. Preferably, a reference subject is a newborn of 1 to 15 days, an infant of 5/6 weeks, an infant of 6 months±1 month, an infant of 1 to 2 years or an adult of over 16 years.

The various parameters of the EMI score can be determined using any of the various methods of skin imaging known to the person of skills in the art. Such methods include, in particular, all the techniques enabling the person of skills in the art to observe and distinguish the cells of the stratum corneum. For example, the skilled person can use any of the microscopy techniques commonly used in the laboratory.

These techniques include, for example, methods of optical microscopy, such as conventional light microscopy, fluorescence microscopy, confocal/multiphoton microscopy and stimulated emission depletion; scanning probe microscopy, including scanning tunneling microscopy (STM), atomic force microscopy (AFM), near-field scanning optical microscopy and others; and electronic microscopy. Electronic microscopy techniques suitable for the method of the invention comprise such techniques as e.g. transmission electron microscopy (TEM), scanning transmission electron microscopy (STEM), focus ion beam microscopy (FIB) and scanning electron microscopy (SEM). Preferably, the Emi score parameters are determined using an electron microscopy technique.

Scanning electron microscopy (SEM) represents a very precise method for direct analysis of the microstructure of the outermost skin layers and stratum corneum in particular. With its resolution and possible magnification from ×100 up to ×100.000 it enables a high quality three-dimensional picture of skin surface topography and ultrastructure. More preferably, the said parameters are determined by performing scanning electron microscopy. According to this embodiment, the various parameters of the EMI score are determined using the image of the skin sample obtained by SEM is thus examined Thus, according to this embodiment, the present invention relates to a method of determining whether the skin surface of a subject is mature or immature in its organisation/function, said method comprising the steps of:
 a) taking a skin sample (A) of the said subject;
 b) obtaining an image of the said skin sample by scanning electron microscopy, and
 c) scoring the said skin sample to an appropriate scale, wherein the said appropriate scale is based on 4 parameters which are the cell density, cell clusters, adhesion/cell shape, and differentiability of single cells.

A "skin sample" according to the invention comprises any sample containing skin cells. Advantageously, the said skin sample is obtained from the surface of the skin by stripping the said surface. Various devices useful for this purpose are commercially available, such as, e.g. the D-SQUAME® Skin Sampling Discs (CuDerm).

The said invention thus enables the person of skills in the art to determine whether a skin surface is mature or not, by taking a skin sample from a subject, performing scanning electron microscopy on the said skin surface sample, and determining the EMI scoring by assessing such parameters as cell density, cell clusters, adhesion/cell shape, and differentiability of single cells.

In addition to the determination of its level of isotropy/anisotropy, the maturation level of the skin can be assessed by examining its topography.

Changes in the function and structure of the skin surface start immediately after birth. In particular, the relief of the skin surface can also be expected to evolve and mature. Indeed, the present inventors have shown that the skin surface topography undergoes rapid maturation and reorganization up until the age of 1-2 years.

Thus, in a preferred embodiment, the method of the invention further comprises a step of assessing the relief of the skin surface.

By "relief" of the skin surface, it is herein understood the elevations and depressions departing from the horizontal plane of the skin. The skin surface relief, or skin surface topography, combines schematically two types of relief, i.e. the microrelief which corresponds to the very fine lines network and the macrorelief which includes deeper wrinkles and furrows.

According to this embodiment, the present invention relates to a method of determining whether the skin surface of a subject is mature or immature in its organisation/function, said method comprising the steps of:
 a) taking a skin sample (A) of the said subject;
 b) obtaining an image of the said skin sample by scanning electron microscopy, c) scoring the said skin sample to an appropriate scale, wherein the said appropriate scale is based on 4 parameters which are the cell density, cell clusters, adhesion/cell shape, and differentiability of single cells, and d) assessing the relief of the skin surface.

Various methods have been developed to analyze the skin surface topography (Levêque, *J Eur Acad Dermatol Venereol*, 12: 103-114, 1999; Tchvialeva et al., in "Skin Roughness Assessment, New Developments in Biomedical Engineering", Domenico Campolo (Ed.), ISBN: 978-953-7619-57-2, InTech, 2010). However, most of them are only qualitative, whereas it is important to have a reliable method which can identify minimal alterations and provide quantitative data. In addition, it is important that the said method enables the simultaneous analyses of the micro- and the macroreliefs.

A quantitative method of cutaneous relief imaging has been developed, wherein the topographical profile is considered as a distribution of heights spaced out at regular intervals (Zahouani and Vargiolu, in "Measuring the Skin", P. Agache Et P. Humbert Eds, Springer, 2004). The said method thus makes use of quantitative parameters which enable monitoring the changes of the skin surface relief. In addition, both micro- and macroreliefs can be analyzed with this method at the same time.

In particular, a parameter associated with the skin surface topography which can be determined by this method is the developed surface (or developed skin surface). This parameter is defined as the ratio between the elementary areas of the interfacial sides and the total surface which constitutes the analyzed area (Zahouani and Vargiolu, in "Measuring the Skin", P. Agache Et P. Humbert Eds, Springer, 2004). In other words, this parameter represents the ratio between the surface of the skin relief, taking into account all the elevations and depressions, and the basic surface of the skin.

It will be immediately be apparent to the person of skills in the art that the higher the developed surface, the more numerous and important the skin surface depressions and elevations are. The developed surface is thus another very good marker of the maturation of the skin.

In fact, the inventors have shown that the rate of increase of the developed skin surface is very high until 1-2 years, showing rapid maturation and reorganization of the skin surface. After 1-2 years, the rate of increase is much slower, indicating that the skin surface is mature.

Thus, in a more preferred embodiment, the method of the invention further comprises a step of assessing the relief of the skin surface, wherein the developed skin surface is determined.

According to this embodiment, the present invention relates to a method of determining whether the skin surface of a subject is mature or immature in its organisation/function, said method comprising the steps of:

a) taking a skin sample (A) of the said subject;

b) obtaining an image of the said skin sample by scanning electron microscopy, c) scoring the said skin sample to an appropriate scale, wherein the said appropriate scale is based on 4 parameters which are the cell density, cell clusters, adhesion/cell shape, and differentiability of single cells, and d) assessing the relief of the skin surface, wherein the said assessment includes determining the developed surface of the said skin sample.

According to a preferred embodiment, the assessment of the relief of the skin surface according to the method of the invention includes a further step prior to the determination of the developed surface of the said skin sample. The said further step consists in transforming the bi-dimensional image in a three-dimensional one. Preferably, in the image transformation of the method, the third dimension is provided by the grey scale of the image.

In order to calculate the developed skin surface of the sample, it is not always possible to determine accurately the basic surface of the sample. Preferably, said basic surface is determined by the root mean square plane method, i.e. establishing the root mean square going through the experimental points. This method aims at minimizing the variations in relation to each of the coefficients of the average plane (Zahouani and Vargiolu, in "Measuring the Skin", P. Agache Et P. Humbert Eds, Springer, 2004).

In order to determine which part of the developed skin surface genuinely represents the maturation of the skin, and not simply the general expansion of the skin as the infant grows, it may be advantageous to normalize the developed skin surface to the body surface area of the subject.

The body surface area is given by the Mosteller formula (Mosteller, *N Engl J Med*, 317(17): 1098, 1987):

$$BSA\ (m^2) = ([Height\ (cm) \times Weight\ (kg)]/3600)^{1/2}$$

More advantageously, the BSA of the subject is normalized to the mean BSA in the adult population, resulting in a correction factor.

The value for the average BSA in the adult population can easily be found in the relevant publications, such as e.g. Verbraecken et al. (*Metabolism*, 55(4): 515-524, 2006).

The corrected developed skin surface is obtained by multiplying the developed skin surface by this correction factor.

According to this embodiment, the present invention relates to a method of determining whether the skin surface of a subject is mature or immature in its organisation/function, said method comprising the steps of:

a) taking a skin sample (A) of the said subject;

b) obtaining an image of the said skin sample by scanning electron microscopy, c) scoring the said skin sample to an appropriate scale, wherein the said appropriate scale is based on 4 parameters which are the cell density, cell clusters, adhesion/cell shape, and differentiability of single cells, d) assessing the relief of the skin surface, wherein the said assessment includes:
   i. determining the developed surface of the said skin sample,
   ii. determining the body surface area (BSA) of the said subject,
   iii. determining the ratio between the BSA of the said subject and the mean BSA value in the adult population, and
   iv. determining the corrected developed skin surface of the said skin sample by multiplying the developed skin sample of step i) by the ratio of step iii).

Functional and structural skin adaptation is a dynamic process which starts immediately after birth in humans, and which involves changes of the barrier function of the skin as the skin matures. It would thus be desirable to use cosmetic products, i.e. active agents, cosmetic raw materials and/or cosmetic formulations, which are suited to the maturation level of the skin.

It will be clear to those skilled in the art that the invention has the advantage of enabling the easy isolation and characterization of active agents, cosmetic raw materials and/or cosmetic formulations. In particular, tolerance, skin penetration and efficiency of an active agent can easily be checked with the method of the invention.

More precisely, the present invention enables to verify that these agents are suited to the maturation stage of the skin surface of a specific class age. In particular, it is important to isolate agents which will reinforce or maintain the barrier organization/function of an immature or moderately mature skin surface, or to maintain the barrier organization/function of a mature skin. For example, it may desirable to isolate agents which will greatly improve the maturation level of the skin in newborns, while agents respecting the skin surface maturation may be convenient for infants of 4-5 years.

In another aspect, the invention thus enables the isolation of active agents having an effect on the skin, particularly on the skin of children, and more particularly on the skin of newborns of 1 to 15 days, infants of 5/6 weeks, infants of 6 months±1 month and infants of 1 to 2 years. Specifically, the identification of the maturation stage of the skin surface according to the method of the invention enables the identification of active agents reinforcing or maintaining the barrier function of the said skin.

The invention therefore also relates to a method for identifying an active agent for the preparation of a cosmetic, pharmaceutical, food and/or nutraceutical composition, said method comprising the steps of:
 a) obtaining at least one sample (A) of skin cells of a subject;
 b) contacting a candidate active agent with the sample (A);
 c) determining the level of maturation of the skin surface of the sample (A) by the method of the invention;
 d) determining the level of maturation of the skin surface in a control sample;
 e) comparing the level of expression of step c) and the level of expression of step d), and
 f) determining whether said candidate active agent is an active agent for the preparation of a dermo-cosmetic pharmaceutical, food and/or nutraceutical composition of the skin of a subject.

According to a preferred embodiment, the subject from whom the sample (A) is obtained is a child. Even more preferably, this subject is a newborn of 1 to 15 days, an infant of 5/6 weeks, an infant of 6 months±1 month or an infant of 1 to 2 years.

The control sample according to the invention is a sample that has not been in contact with the candidate active agent, thus allowing a significant comparison between the skin surface maturation level of step c) and that of step d). For example, the sample (A) that has not been contacted with the candidate can be used as a control. In this case, the maturation of the skin surface is evaluated in the sample (A) before and after being brought into contact with the candidate active agent.

The candidate is an active agent for preparing a cosmetic composition for the skin, if said active agent maintains or improves the maturation level of the skin surface.

Preferably, the active agent of the invention is capable of restoring the normal level of skin maturation. By "normal level", it is herein referred to the level of maturation of the skin surface commonly observed in a population of healthy subjects of the same age as the subject. In other words, the surface of the treated skin shows a degree of isotropy which is the same as the one observed in a population of healthy subjects of the same age. In still other words, the EMI score is the same as the one observed in a population of healthy subjects of the same age. More preferably, the surface of the treated skin shows a degree of isotropy and a topography which are the same as the ones observed in a population of healthy subjects of the same age. In yet other words, the EMI score and the developed surface are the same as the ones observed in a population of healthy subjects of the same age.

Alternatively, the active agent of the invention is capable of leading to an improved level of skin maturation. By "improved level", it is herein referred to the level of maturation of the skin surface commonly observed in a population of healthy subjects of the same age as the subject. In other words, the surface of the treated skin shows a degree of isotropy higher than the one observed in a population of healthy subjects of the same age. In still other words, the EMI score is superior to the one observed in a population of healthy subjects of the same age. More preferably, the surface of the treated skin shows a degree of isotropy higher, and a topography more developed than the ones observed in a population of healthy subjects of the same age. In yet other words, the EMI score and the developed surface are superior to the ones observed in a population of healthy subjects of the same age.

In another aspect, the invention enables the isolation of raw materials, which can be used in the development of formulations for the skin, particularly for the skin of the child, and, more particularly, for the skin of newborns of 1 to 15 days, infants of 5/6 weeks, infants of 6 months±1 month and infants of 1 to 2 years. A formulation of the invention is a preparation obtained by mixing different raw materials, to meet a demand expressed generally in terms of properties. The formulations of the invention can be used in cosmetics, pharmaceutical, food and/or nutraceutical. They can be used in humans or animals, by oral or topical application.

The invention thus enables the identification of raw materials increasing tolerance and skin penetration. The determination of the skin maturation level according to the method of the invention allows the identification of raw materials or not modulating the said maturation.

The invention therefore also relates to a method for identifying a raw material that can be used for the preparation of a cosmetic, pharmaceutical, food and/or nutraceutical formulation, said method comprising the steps of:
 a) obtaining at least one skin sample (A) from a subject;
 b) contacting a candidate raw material with the sample (A);
 c) determining the level of maturation of the skin surface of the sample (A) by the method of the invention;
 d) determining the level of maturation of the skin surface of a control sample;
 e) comparing the level of maturation of step c) and the level of maturation of step d), and
 f) determining if said material is a candidate material for the preparation of a cosmetic, pharmaceutical, food and/or nutraceutical formulation.

According to a preferred embodiment, the subject from whom the sample (A) is obtained is a child. Even more preferably, this subject is a newborn of 1 to 15 days, an infant of 5/6 weeks, an infant of 6 months±1 month, or an infant of 1 to 2 years.

The control sample according to the invention is a sample that has not been in contact with the candidate raw material, thus allowing a significant comparison between the skin surface maturation level of step c) and that of step d). For example, the sample (A) that has not been contacted with the candidate raw material can be used as a control. In this case, the maturation of the skin surface is evaluated in the sample (A) before and after being brought into contact with the candidate raw material.

As explained hereabove, it is important that the agents, raw materials or formulations of the invention are suited to the maturation stage of the skin surface of a specific class age. Thus, in a preferred embodiment, the active agent, raw material, or cosmetic, pharmaceutical, food and/or nutraceutical formulation of the invention accompanies, protects, or restores the maturation of the skin.

It is clear that the invention thus not only enables the isolation and characterization of raw materials that can be used in cosmetic, pharmaceutical, food and/or nutraceutical formulations, but also to test said formulations already made and to identify those that have optimal qualities of tolerance, efficacy, toxicology and skin penetration vis-à-vis a subject's skin, especially a child's skin. In particular, those skilled in the art will understand readily that that the identification of the maturation level of the surface of the skin according to the method of the invention is crucial in determining whether a formulation can be used on the skin of children.

The invention therefore also relates to a method for identifying a cosmetic, pharmaceutical, food and/or nutraceutical formulation for the skin, said method comprising the steps of:
 a) obtaining at least one sample (A) of skin cells of a subject;
 b) contacting a candidate active formulation with the sample (A);
 c) determining the level of maturation of the skin surface of the sample (A) by the method of the invention;
 d) determining the level of maturation of the skin surface in a control sample;
 e) comparing the level of maturation of step c) and the level of maturation of step d), and
 f) determining whether said candidate formulation is a cosmetic, pharmaceutical, food and/or nutraceutical formulation.

According to a preferred embodiment, the subject from whom the sample (A) is obtained is a child. Even more preferably, this subject is a newborn of 1 to 15 days, an infant of 5/6 weeks, an infant of 6 months±1 month, or an infant of 1 to 2 years.

The control sample according to the invention is a sample that has not been in contact with the candidate formulation, thus allowing a significant comparison between the skin surface maturation level of step c) and that of step d). For example, the sample (A) that has not been contacted with the candidate formulation can be used as a control. In this case, the maturation of the skin surface is evaluated in the sample (A) before and after being brought into contact with the candidate formulation.

In another aspect, the invention relates to a method for assessing the tolerance of a cosmetic, pharmaceutical, food and/or nutraceutical composition, said method comprising the steps of:
 a) obtaining at least one sample (A) of skin cells of a subject;
 b) contacting a candidate active agent with the sample (A);
 c) determining the level of maturation of the skin surface of the sample (A) by the method of the invention;
 d) determining the level of maturation of the skin surface in a control sample;
 e) comparing the level of expression of step c) and the level of expression of step d), and
 f) determining whether said cosmetic, pharmaceutical, food and/or nutraceutical composition of the skin of a subject is tolerated by the skin of the subject.

According to a preferred embodiment, the subject from whom the sample (A) is obtained is a child. Even more preferably, this subject is a newborn of 1 to 15 days, an infant of 5/6 weeks, an infant of 6 months±1 month or an infant of 1 to 2 years.

The control sample according to the invention is a sample that has not been in contact with the candidate active agent, thus allowing a significant comparison between the skin surface maturation level of step c) and that of step d). For example, the sample (A) that has not been contacted with the candidate can be used as a control. In this case, the maturation of the skin surface is evaluated in the sample (A) before and after being brought into contact with the candidate active agent.

According to another aspect of the invention, the level of maturation of the skin surface can be used to characterize skin disorders. Specifically, it is possible to characterize, using said maturation level of the invention, skin diseases affecting newborns, infants, children whose age is between 2 and 16, and/or adults.

By "skin disorder", it is herein referred to all abnormal reactions that can affect the skin of an individual. These conditions affect both the skin itself (that is to say, the epidermis, dermis and/or hypodermis), the pores of the skin, sweat and sebaceous glands attached thereto, hair or nails.

Skin disorders according to the invention result in injuries, which corresponds to a damaged skin or a skin in poor condition. Damaged skin includes such reactive sensitive skin, dry skin, skin damaged by the sun, by radiation, by the cold, by stress or pollution, by an allergy, urticaria, eczema and by other forms of dermatitis such as atopic dermatitis, impetigo, irritative dermatitis, particularly irritant dermatitis of the seat or diaper rash, contact dermatitis, seborrheic dermatitis of the skin and scalp (cradle cap), psoriasis, disease-Lainer Moussous, or through wounds or burns. Skin disorder is therefore meant to include disorders as diverse as herpes, angiomas (including tuberous, subcutaneous or plans), hemangiomas, baby acne, adolescent acne, ichthyoses (e.g. vulgaris, congenital, lamellaris . . . ) etc. A skin disorder can be caused or exacerbated by an external infection example of parasitic, viral, bacterial or fungal. The term "skin disorder" as used herein is also meant to encompass as well the warts, strophulus prurigo, scabies, head lice, or fungal infections. The latter are caused by parasitic fungi proliferation of parasites in the body. The most common fungal infections comprise candidiasis and pityrosporoses, which are caused by yeast overgrowth of the skin.

Such skin disorders can have potentially deleterious effects on the skin barrier function, as is the case for, e.g., dry skin. Such effects would translate into an alteration of the maturation level of the skin surface.

As is also known to the skilled person, some general diseases may also be manifested by symptoms affecting the skin. For example, dermatitis or rash is known to be caused by a great variety of diseases. As explained above, dermatitis may occur with viral infections, such as herpes zoster; fungal infections, such as a yeast infection (Candida albicans); bacterial infections, such as impetigo; and sexually transmitted infections (STIs). But it may also occur as a symptom of a more serious disease, such as liver disease, kidney disease, or some types of cancer. Dermatitis may also appear as a side effect to some medicines. A very rare and serious type of generalized red rash called toxic epidermal necrolysis (TEN) may occur after using sulfa drugs and can cause the skin to peel away, leaving large areas of tissue that weep or ooze fluid like a severe burn.

According to this particular embodiment, the invention provides a method of determining if a skin disorder or a general disease affects the maturation of the skin surface, said method comprising the following steps:
- a) obtaining at least one skin sample (A') of cells of a subject affected by said skin disorder or general disease;
- b) obtaining at least one control sample (B) of skin cells of a healthy subject;
- c) determining the level of maturation of the skin surface of the sample (A') by the method of the invention;
- d) determining the level of maturation of the skin surface of the sample of step b) by the method of the invention;
- e) comparing the level of maturation of step a) and the level of maturation of step b), and
- f) determining whether the level maturation of the skin surface is affected by the said skin disorder or general disease.

According to a preferred embodiment, the subject from whom the sample (A) is obtained is a child. Even more preferably, this subject is a newborn of 1 to 15 days, an infant of 5/6 weeks, an infant of 6 months±1 month, an infant of 1 to 2 years.

It will be immediately clear to the person of skills in the art that the effect of a skin disorder on the maturation of the skin surface is immediately advantageous for isolating agents active in treating the said disorder.

The invention therefore also relates to a method for identifying an active agent for treating a particular skin disorder, said method comprising the steps of:
- a) obtaining at least one skin sample (A') from a subject affected by said skin disorder;
- b) contacting a candidate agent with the said sample (A');
- c) determining the level of maturation of the skin surface of the sample (A') by the method of the invention;
- d) determining the level of maturation of the skin surface of at least one control sample;
- e) comparing the level of maturation of step c) and the level of maturation of step d), and
- f) determining if said candidate is an active agent for treating skin disorders.

According to a preferred embodiment, the subject from whom the sample (A) is obtained is a child. Even more preferably, this subject is a newborn of 1 to 15 days, an infant of 5/6 weeks, an infant of 6 months±1 month, or an infant of 1 to 2 years.

Preferably, the active agent of the invention is capable of restoring the normal level of skin maturation. By "normal level", it is herein referred to the level of maturation of the skin surface commonly observed in a population of healthy subjects of the same age as the patient affected by the said disorder. In other words, the surface of the treated skin shows a degree of isotropy which is the same as the one observed in a population of healthy subjects of the same age. In still other words, the EMI score is the same as the one observed in a population of healthy subjects of the same age. More preferably, the surface of the treated skin shows a degree of isotropy and a topography which are the same as the ones observed in a population of healthy subjects of the same age. In yet other words, the EMI score and the developed surface are the same as the ones observed in a population of healthy subjects of the same age.

Alternatively, the active agent of the invention is capable of leading to an improved level of skin maturation. By "improved level", it is herein referred to the level of maturation of the skin surface commonly observed in a population of healthy subjects of the same age as the patient affected by the said disorder. In other words, the surface of the treated skin shows a degree of isotropy higher than the one observed in a population of healthy subjects of the same age. In still other words, the EMI score is superior to the one observed in a population of healthy subjects of the same age. More preferably, the surface of the treated skin shows a degree of isotropy higher, and a topography more developed than the ones observed in a population of healthy subjects of the same age. In yet other words, the EMI score and the developed surface are superior to the ones observed in a population of healthy subjects of the same age.

The examples that follow are merely exemplary of the scope of this invention and content of this disclosure. One skilled in the art can devise and construct numerous modifications to the examples listed below without departing from the scope of this invention.

FIGURE LEGENDS

FIG. 1: SEM pictures of the stratum corneum layer in the different groups.

Figure 2:
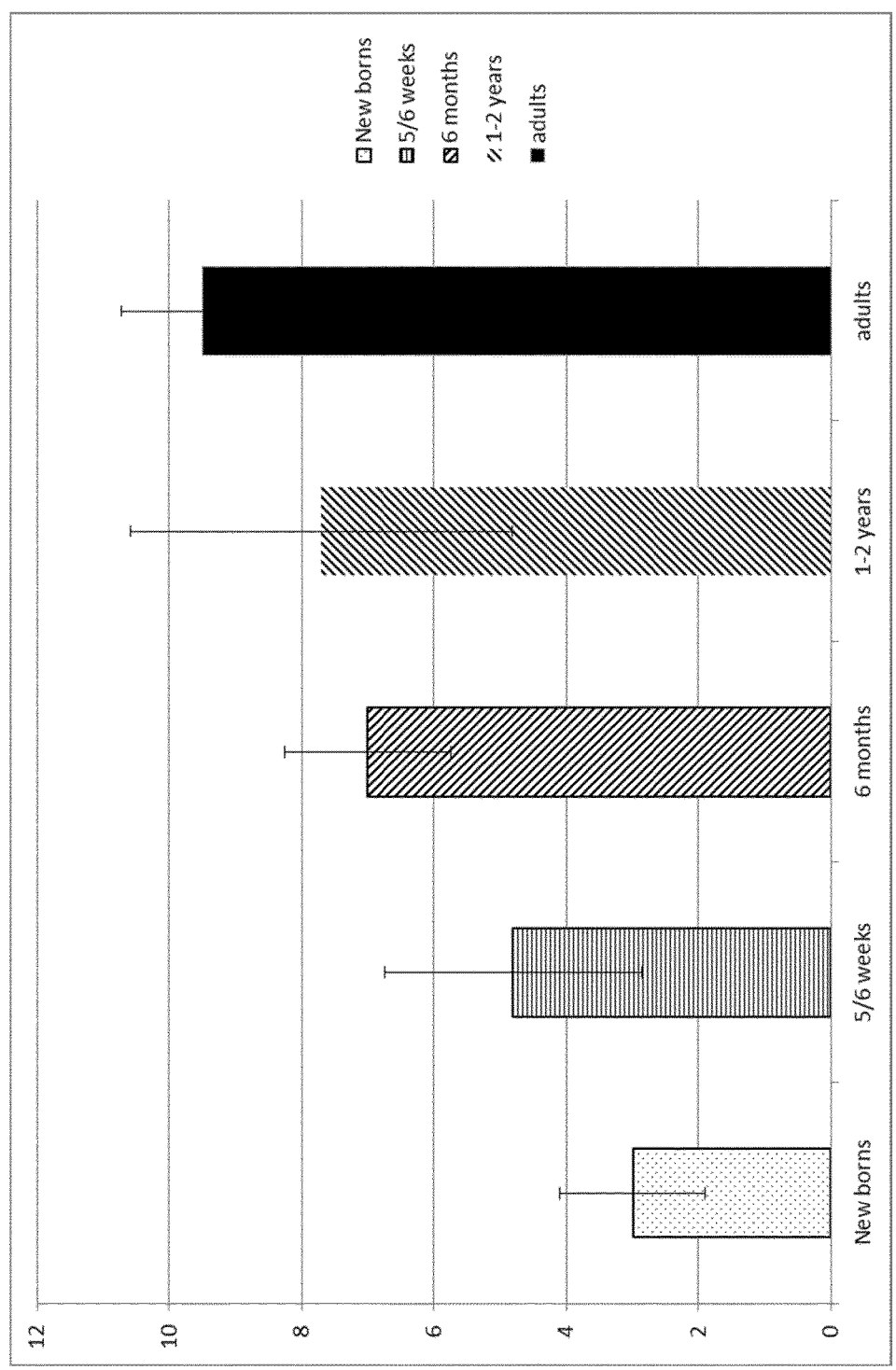

FIG. 2: Correlation between the age and the EMI score.

Figure 3:
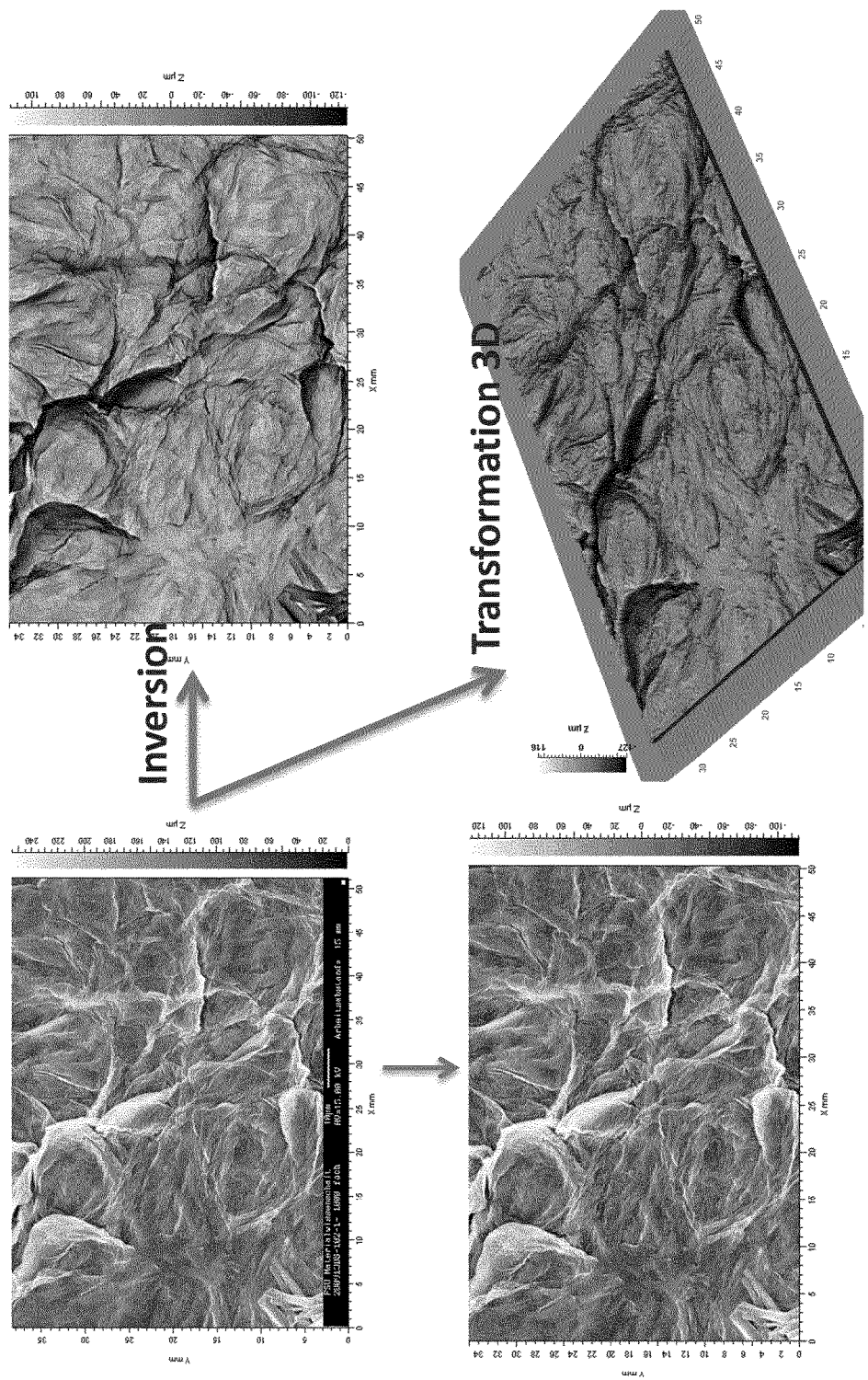

FIG. 3: Methodology of SEM image quantification

Figure 4:
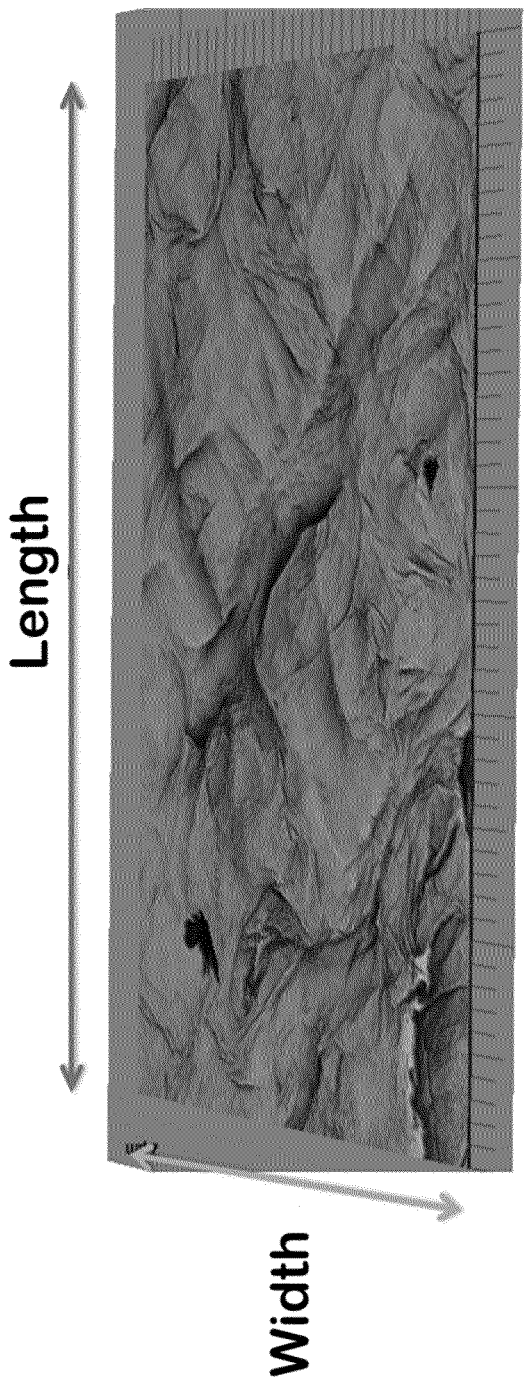
Figure 4:
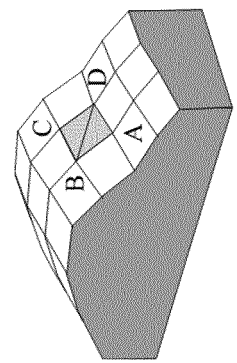

FIG. 4: Developed surface.

Figure 5:
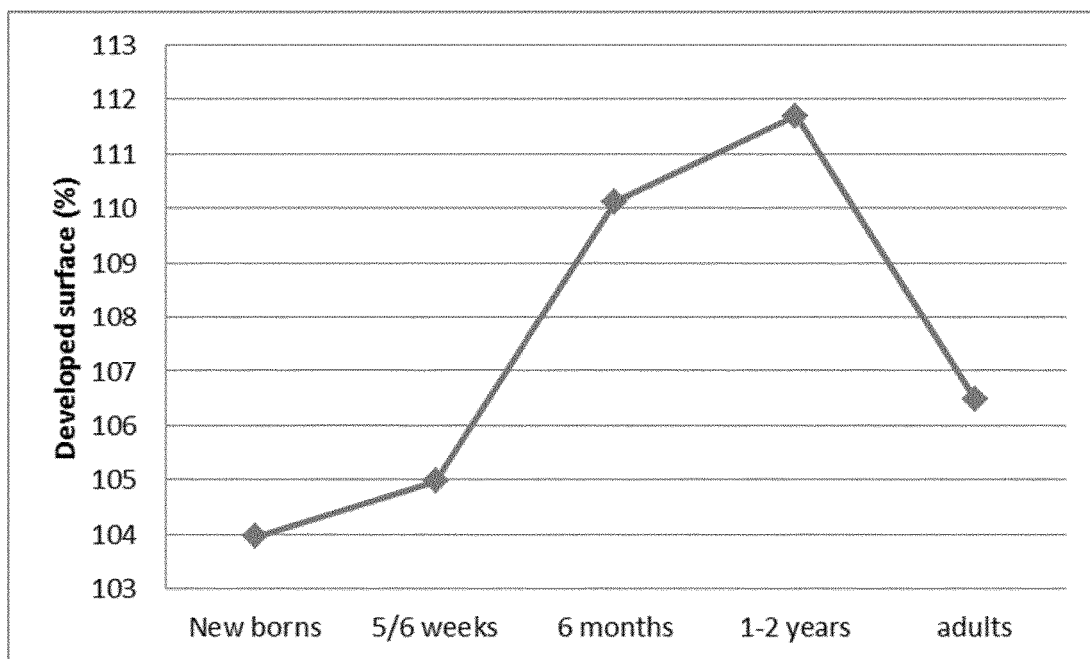

FIG. 5: Evolution of the developed surface as a function of the age of the children.

Figure 6:
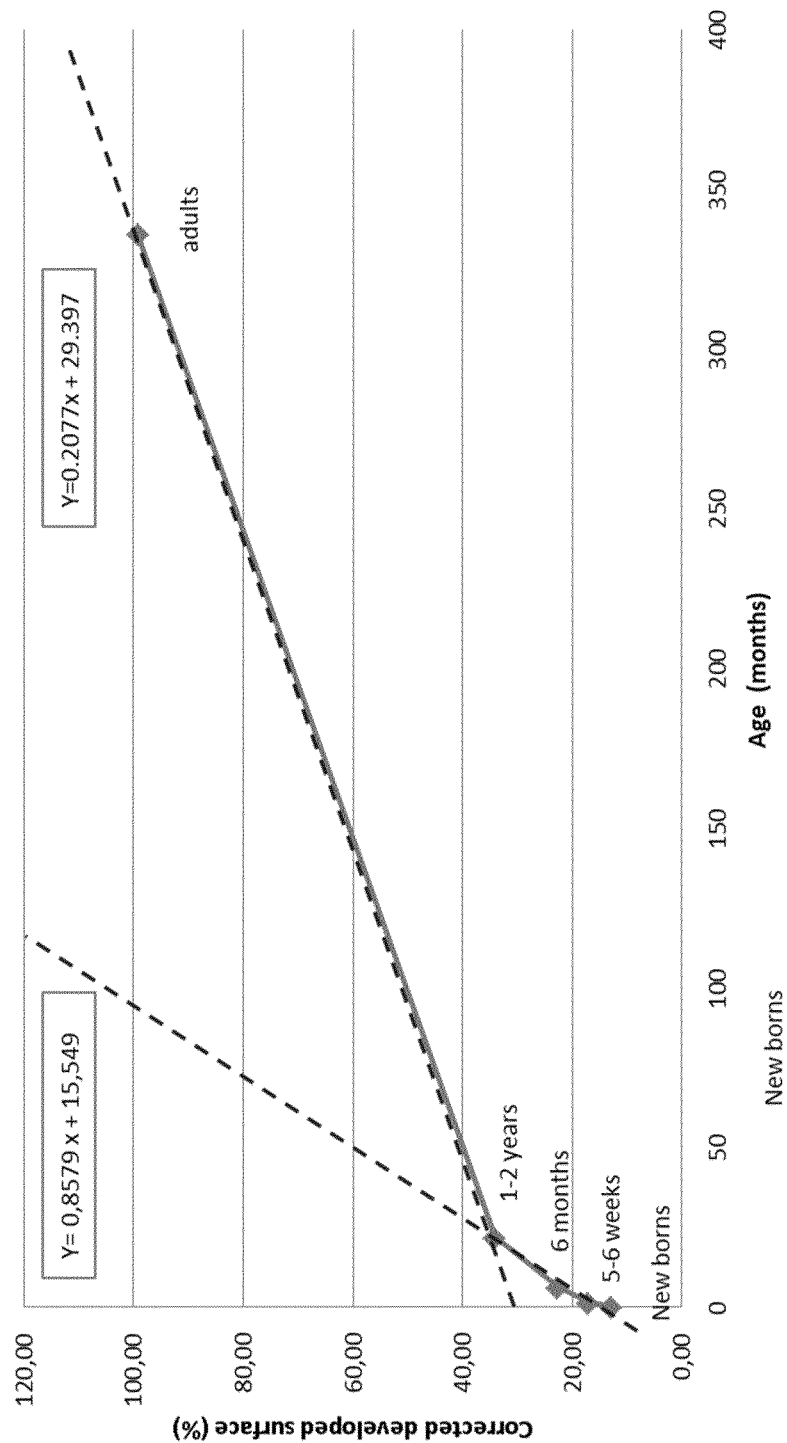

FIG. 6: Evolution of the corrected developed surface as a function of the age of the children.

EXPERIMENTAL EXAMPLE

In the study, adhesive tapes were collected on the volar forearm in 36 healthy male and female volunteers in 6 age groups (n=6; each group) newborns (1-15 days), 5 weeks, 6 months, 1-2 years., and adults 20-35 years old (Table 1). In the second, confirmatory trial 30 volunteers in the same age groups with n=6 per group were analyzed without the newborn group. The corneocytes attached to the D-Squames were analyzed subsequently by scanning electron microscopy (SEM).

Based on print-outs of the SEM pictures a surface score was developed with the following parameters: Cell density, cluster formation, adhesion/cell shape and differentiability of single cells at magnifications of 30× and 500× with three different grading steps for each parameter (FIG. 1, Table 2).

TABLE 1

Summary of subject demographic characteristics

| Age group | N | Mean ± SD | Median | Min. max |
|---|---|---|---|---|
| 1 to 15 days (new borns) | 6 | 8.7 ± 4.4 (days) | 9.0 (days) | 3.0, 14 |
| 5 weeks + 1 week | 6 | 5.9 ± 0.7 (weeks) | 6.0 (weeks) | 5.0, 6.0 |
| 6 months ± 1 month | 6 | 6.2 ± 0.4 (months) | 6.0 (months) | 6.0, 7.0 |
| 1 to 2 years | 6 | 22.7 ± 6.2 (months) | 18.0 (months) | 18.0, 30.0 |
| 20-35 years | 6 | 28.0 ± 5.0 (years) | 27.5 (years) | 20.0, 35.0 |

TABLE 2

E.M.I Score

| | 30x | | 500x Differentiability of single cells |
|---|---|---|---|
| | Cell density | Clusters | Adhesion/cell shape | |

| | Cell density | Clusters | Adhesion/cell shape | Differentiability of single cells |
|---|---|---|---|---|
| 0 | Separated | Completely irregular clusters | Asymmetry completely irregular | Cells not differentiable |
| 1 | Clustered Dispersed | Mixture of regular and irregular clusters | Partially symmetric Partially regular | Cells partially differentiable |
| 2 | Evenly dispersed Almost confluent | Almost regular clusters | Mostly symmetric Mostly regular | Cells mostly differentiable |
| 3 | Confluent | Regular clusters | Symmetry Regular cell shape Identical in all geometric directions Octogonal cells Regular surface | Cells easily differentiable |

We developed a score that allows the semi-quantitative analysis of surface isotropy (Table 3).

TABLE 3

E.M.I. Scoring

| Sum Score | Score points | Maturity |
|---|---|---|
| Anisotropy | 0-4 | immature |
| Intermedium isotropy | 5-7 | |
| Good isotropy | 8-12 | mature |

We were able to show a correlation between increasing age and the score (FIG. 2).

TABLE 4

Summary of scoring of SEM

| Age group | N | Mean ± SD | Median | Significativity vs adult group * [20-35 year] |
|---|---|---|---|---|
| 1 to 15 days (newborns) | 6 | 3 ± 1.10 | 3.0 | S (p < 0.0001) |
| 5 weeks + 1 week | 6 | 4.8 ± 1.94 | 4.5 | S (p = 0.0001) |
| 6 months ± 1 month | 6 | 7.0 ± 1.26 | 7.5 | S (P = 0.0246) |
| 1 to 2 years | 6 | 7.7 ± 2.88 | 7.5 | NS |
| 20-35 years | 6 | 9.5 ± 1.22 | 10.0 | — |

* two sided t-test, p < 0.05

The EMI score—based on the non-invasively removed surface corneocytes represents a new method to analyze the skin surface micro-topography at different age groups.

We could show a correlation between the EMI score values and increasing age (Table 4). This is indicative of being a marker of skin maturation and is probably related to the organization of the skin micro-anatomy after birth.

In order to obtain a more detailed overview of the maturation of the skin surface, the topography of the skin surface was assessed in the population of each age group.

SEM pictures (magnification ×1000) were used to calculate the developed surface as described in Zahouani and Vargiolu (in "Measuring the Skin", P. Agache Et P. Humbert Eds, Springer, 2004).

First, two-dimensional images were transformed into three-dimensional images, by using grey levels as the third dimension (FIG. 3).

Then, the developed surface (FIG. 4) was calculated using the equation:

$$S_{Dev} = \frac{\sum_{j=1}^{N-1} \sum_{i=1}^{M-1} A_{ij}}{\text{Length} \times \text{Width}}$$

The resulting value showed a bell-shape distribution, with a peak at around 1-2 years (FIG. 5). This suggested a change in the maturation rate of the skin surface when children reached that age.

In order to confirm that this effect was not simply reflecting the general expansion of the skin surface, but was genuinely indicating an effect on the skin surface topography, the developed surface was linearized by a correction factor.

First, the body surface area in each age group was calculated according to the Mosteller formula (Mosteller, N Eng J Med, 317(17): 1098, 1987) using the mean height and weight of the said age group (Table 5):

$$BSA\ (m^2) = ([Height\ (cm) \times Weight\ (kg)]/3600)^{1/2}$$

TABLE 5

| Group | Enrolled subjects | Age (months) Mean (SD) | Weight (kg) Mean (SD) | Height (cm) Mean (SD) |
|---|---|---|---|---|
| Newborns | 6 | 0.29 | 3.1 (0.6) | 50.2 (2.6) |
| 5/6 weeks | 6 | 1.475 | 4.7 (0.6) | 55.7 (3.1) |
| 6 months | 6 | 6.2 | 7.9 (1.3) | 70.2 (4.4) |
| 1/2 years | 6 | 22.7 | 12.4 (2.5) | 85.8 (9.8) |
| adults | 6 | 336 | 59.6 (5.7) | 166 (4.1) |

All the BSA values were then normalized to the BSA of the adults, giving a correction factor which in turn used to correct the developed surface values (Table 6). The corrected developed surface values thus genuinely reflect changes in the topography of the skin surface.

TABLE 6

| Age group | Developed surface | BSA | Correction factor | Corrected developed surface |
|---|---|---|---|---|
| Newborns | 103.96 | 0.21 | 0.13 | 13.04 |
| 5/6 weeks | 104.98 | 0.27 | 0.16 | 17.08 |
| 6 months | 110.11 | 0.39 | 0.22 | 24.28 |
| 1/2 years | 111.69 | 0.54 | 0.31 | 34.11 |
| adults | 106.49 | 1.66 | 0.93 | 99.18 |

FIG. 6 shows the increase in the corrected developed surface area as a function of age. Two rates of development can clearly be observed. The developed surface grows very fast until 1-2 years indicating a strong maturation of the skin surface (rate=0.8579). In individuals older than 1-2 years, the maturation is slower (rate=0.2077).

The developed surface corresponds to the organization of the skin within a specific surface. This organization could be seen as a "grid" of elevations and depressions. The present results could thus indicate that a "grid" is initially constructed very fast and becomes denser and denser, until the individual reaches 1-2 years old. This initial phase would then be followed by a phase of slow, but regular, construction of the "grid".

The invention claimed is:

1. A method of determining whether the skin surface of a subject is mature or immature in its organisation/function, said method comprising:
   a) taking a skin sample (A) of said subject by stripping the skin surface;
   b) obtaining an image of said skin sample using scanning electron microscopy;
   c) scoring 4 parameters on said skin sample, which are:
      (i) cell density, wherein this parameter is scored on a scale of 0 to 3, where 0 indicates that cells are separated, 1 indicates that cells are clustered/dispersed, 2 indicates that cells are evenly dispersed/almost confluent, and 3 indicates that cells are confluent;
      (ii) cell clusters, wherein this parameter is scored on a scale of 0 to 3, where 0 indicates that clusters are completely irregular, 1 indicates that cell clusters are a mixture of regular and irregular clusters, 2 indicates that cells are almost regular clusters, and 3 indicates that clusters are regular;
      (iii) adhesion/cell shape, wherein this parameter is scored on a scale of 0 to 3, where 0 indicates that the shape of the cells is asymmetric and completely irregular, 1 indicates that the shape of the cells is partially symmetric and partially regular, 2 indicates that the shape of the cells is mostly symmetrical and mostly regular, and 3 indicates that the shape of the cells is regular and symmetrical; and
      (iv) differentiability of single cells, wherein this parameter is scored on a scale of 0 to 3, where 0 indicates that cells are not differentiable, 1 indicates that the cells are partially differentiable, 2 indicates that the cells are mostly differentiable, and 3 indicates that cells are easily differentiable;
   d) determining skin maturity level of the subject by scoring said skin sample from 0 to 12 based on the sum of the scores for said 4 parameters; and
   e) applying to the subject a cosmetic product suited to the maturation level of the skin, wherein the cosmetic product is selected from the group consisting of an active agent, a cosmetic raw material and/or a cosmetic formulation;
   wherein a score of 0 indicates that the properties of the skin in said skin sample are directionally dependent (strong anisotropy) and a score of 12 indicates the properties of the skin in said skin sample are identical in all directions (good isotropy); and
   wherein said subject is a newborn of 1 to 15 days, an infant of 5 to 6 weeks, an infant of 6 months±1 month, an infant of 1 to 2 years, or a child up to 16 years.

2. The method of claim 1, further comprising a step of assessing the relief of the skin surface.

3. The method of claim 2, wherein said assessment includes determining the developed surface of said skin sample.

4. The method of claim 3, wherein said assessment includes a further step of determining the body surface area (BSA) of said subject.

5. The method of claim 4, wherein said assessment includes the further steps of determining the ratio between the BSA of said subject and the average BSA value in the adult population, and determining the corrected developed skin surface of said skin sample by multiplying the developed surface of said skin sample of step b) by said ratio.

6. The method of claim 1, wherein the third dimension in step c) is provided by the grey scale of the image.

7. A method of determining whether the skin surface of a subject is mature or immature in its organisation/function, said method comprising:
   a) taking a skin sample (A) of said subject by stripping the skin surface;
   b) obtaining an image of said skin sample using scanning electron microscopy;
   c) transforming the obtained image from bi-dimensional to three-dimensional;
   d) scoring 4 parameters on said skin sample, which are:
      (i) cell density, wherein this parameter is scored on a scale of 0 to 3, where 0 indicates that cells are separated, 1 indicates that cells are clustered/dispersed, 2 indicates that cells are evenly dispersed/almost confluent, and 3 indicates that cells are confluent;
      (ii) cell clusters, wherein this parameter is scored on a scale of 0 to 3, where 0 indicates that clusters are completely irregular, 1 indicates that cell clusters are a mixture of regular and irregular clusters, 2 indicates that cells are almost regular clusters, and 3 indicates that clusters are regular;
      (iii) adhesion/cell shape, wherein this parameter is scored on a scale of 0 to 3, where 0 indicates that the shape of the cells is asymmetric and completely irregular, 1 indicates that the shape of the cells is partially symmetric and partially regular, 2 indicates that the shape of the cells is mostly symmetrical and mostly regular, and 3 indicates that the shape of the cells is regular and symmetrical; and
      (iv) differentiability of single cells, wherein this parameter is scored on a scale of 0 to 3, where 0 indicates that cells are not differentiable, 1 indicates that the cells are partially differentiable, 2 indicates that the cells are mostly differentiable, and 3 indicates that cells are easily differentiable; and
   e) determining skin maturity level of the subject by scoring said skin sample from 0 to 12 based on the sum of the scores for said 4 parameters;
   wherein a score of 0 indicates that the properties of the skin in said skin sample are directionally dependent (strong anisotropy) and a score of 12 indicates the properties of the skin in said skin sample are identical in all directions (good isotropy); and
   wherein said subject is a newborn of 1 to 15 days, an infant of 5 to 6 weeks, an infant of 6 months±1 month, an infant of 1 to 2 years, or a child up to 16 years.

8. The method of claim 7, further comprising a step of assessing the relief of the skin surface.

9. The method of claim 8, wherein said assessment includes determining the developed surface of said skin sample.

10. The method of claim 9, wherein said assessment includes a further step of determining the body surface area (BSA) of said subject.

11. The method of claim 10, wherein said assessment includes the further steps of determining the ratio between the BSA of said subject and the average BSA value in the adult population, and determining the corrected developed skin surface of said skin sample by multiplying the developed surface of said skin sample of step b) by said ratio.

12. A method of determining whether the skin surface of a subject is mature or immature in its organisation/function, said method comprising:
   a) taking a skin sample (A) of said subject by stripping the skin surface;
   b) obtaining an image of said skin sample using scanning electron microscopy;
   c) transforming the obtained image from bi-dimensional to three-dimensional;
   d) scoring 4 parameters on said skin sample, which are:
      (i) cell density, wherein this parameter is scored on a scale of 0 to 3, where 0 indicates that cells are separated, 1 indicates that cells are clustered/dispersed, 2 indicates that cells are evenly dispersed/almost confluent, and 3 indicates that cells are confluent;
      (ii) cell clusters, wherein this parameter is scored on a scale of 0 to 3, where 0 indicates that clusters are completely irregular, 1 indicates that cell clusters are a mixture of regular and irregular clusters, 2 indicates that cells are almost regular clusters, and 3 indicates that clusters are regular;
      (iii) adhesion/cell shape, wherein this parameter is scored on a scale of 0 to 3, where 0 indicates that the shape of the cells is asymmetric and completely irregular, 1 indicates that the shape of the cells is partially symmetric and partially regular, 2 indicates that the shape of the cells is mostly symmetrical and mostly regular, and 3 indicates that the shape of the cells is regular and symmetrical; and
      (iv) differentiability of single cells, wherein this parameter is scored on a scale of 0 to 3, where 0 indicates that cells are not differentiable, 1 indicates that the cells are partially differentiable, 2 indicates that the cells are mostly differentiable, and 3 indicates that cells are easily differentiable;
   e) determining skin maturity level of the subject by scoring said skin sample from 0 to 12 based on the sum of the scores for said 4 parameters; and
   f) applying to the subject a cosmetic product suited to the maturation level of the skin, wherein the cosmetic product is selected from the group consisting of an active agent, a cosmetic raw material and/or a cosmetic formulation;
   wherein a score of 0 indicates that the properties of the skin in said skin sample are directionally dependent (strong anisotropy) and a score of 12 indicates the properties of the skin in said skin sample are identical in all directions (good isotropy); and
   wherein said subject is a newborn of 1 to 15 days, an infant of 5 to 6 weeks, an infant of 6 months±1 month, an infant of 1 to 2 years, or a child up to 16 years.

13. The method of claim 12, further comprising a step of assessing the relief of the skin surface.

14. The method of claim 13, wherein said assessment includes determining the developed surface of said skin sample.

15. The method of claim 14, wherein said assessment includes a further step of determining the body surface area (BSA) of said subject.

16. The method of claim 15, wherein said assessment includes the further steps of determining the ratio between the BSA of said subject and the average BSA value in the adult population, and determining the corrected developed skin surface of said skin sample by multiplying the developed surface of said skin sample of step b) by said ratio.

17. The method of claim 12, wherein the third dimension in step c) is provided by the grey scale of the image.

* * * * *